United States Patent
Doerr et al.

(10) Patent No.: US 8,509,896 B2
(45) Date of Patent: Aug. 13, 2013

(54) BIVENTRICULAR CARDIAC STIMULATOR

(75) Inventors: Thomas Doerr, Berlin (DE); Dirk Muessig, West Linn (DE); Volker Lang, West Linn (DE)

(73) Assignee: Biotronik CRM Patent AG, Baar (CH)

( * ) Notice: Subject to any disclaimer, the term of this patent is extended or adjusted under 35 U.S.C. 154(b) by 1309 days.

(21) Appl. No.: 12/269,746

(22) Filed: Nov. 12, 2008

(65) Prior Publication Data

US 2009/0125077 A1 May 14, 2009

(30) Foreign Application Priority Data

Nov. 14, 2007 (DE) .......................... 10 2007 054 178

(51) Int. Cl.
*A61N 1/365* (2006.01)
(52) U.S. Cl.
USPC .......................................................... 607/25
(58) Field of Classification Search
None
See application file for complete search history.

(56) References Cited

U.S. PATENT DOCUMENTS

| | | | |
|---|---|---|---|
| 6,285,907 B1 * | 9/2001 | Kramer et al. | 607/9 |
| 6,477,417 B1 * | 11/2002 | Levine | 607/9 |
| 6,477,420 B1 * | 11/2002 | Struble et al. | 607/14 |
| 6,567,700 B1 | 5/2003 | Turcott | |
| 6,668,194 B2 * | 12/2003 | VanHout | 607/9 |
| 7,043,301 B1 | 5/2006 | Kroll et al. | |
| 7,187,972 B1 * | 3/2007 | Fain et al. | 607/14 |
| 2004/0049236 A1 * | 3/2004 | Kramer et al. | 607/9 |
| 2004/0143299 A1 * | 7/2004 | Casavant et al. | 607/9 |
| 2004/0193223 A1 * | 9/2004 | Kramer et al. | 607/9 |
| 2004/0215245 A1 | 10/2004 | Stahmann et al. | |
| 2004/0215257 A1 | 10/2004 | Van Oort et al. | |
| 2005/0137630 A1 * | 6/2005 | Ding et al. | 607/9 |
| 2007/0150015 A1 | 6/2007 | Zhang et al. | |
| 2008/0009910 A1 | 1/2008 | Kraetschmer | |
| 2008/0097536 A1 * | 4/2008 | Kramer et al. | 607/9 |
| 2008/0146934 A1 | 6/2008 | Czygan et al. | |

OTHER PUBLICATIONS

European Search Report, dated Mar. 3, 2009, 8 pages.
German Search report, dated Sep. 19, 2008, 4 pages.

* cited by examiner

*Primary Examiner* — Carl H Layno
*Assistant Examiner* — Paula J Stice
(74) *Attorney, Agent, or Firm* — ARC IP Law, PC; Joseph J. Mayo

(57) ABSTRACT

An implantable cardiac stimulator (10), configured to switch mode of operation between at least one right ventricular stimulation mode in which no control signals triggering left ventricular stimulation pulses are delivered to the left ventricular stimulation unit and a biventricular stimulation mode in alternation. Switching takes place as a function of duration of prevailing QRS signal interval, such that the cardiac stimulator switches to biventricular stimulation mode when comparison of the duration of a prevailing QRS signal interval with a first comparison value reveals the duration of the prevailing QRS signal interval is longer than a first reference value represented by the first comparison value and switches to right ventricular stimulation mode when comparison of the duration of a prevailing QRS signal interval with a second comparison value reveals the duration of the prevailing QRS signal interval is shorter than a second reference value represented by the second comparison value.

15 Claims, 9 Drawing Sheets

BIVENTRICULAR CARDIAC STIMULATOR

This application takes priority from German Patent Application DE 10 2007 054 178.5, filed 14 Nov. 2007, the specification of which is hereby incorporated herein by reference.

BACKGROUND OF THE INVENTION

1. Field of the Invention

The invention relates to an implantable cardiac stimulator for cardiac resynchronization therapy (CRT) on a heart. The cardiac stimulator may be a cardiac pacemaker or an implantable cardioverter/defibrillator (ICD) or a combination of the two that is capable of stimulating both ventricles of a heart.

2. Description of the Related Art

Such a cardiac stimulator typically has at least one right ventricular sensing unit and one right ventricular stimulation unit as well as one left ventricular sensing unit and one left ventricular stimulation unit. During operation of the cardiac stimulator, these units are each connected to electrodes implanted at suitable locations in the heart. The electrode line with the electrodes for detecting electric potentials in the left ventricle of the heart and for delivering left ventricular stimulation pulses is typically part of a left ventricular electrode line, which is implanted through the coronary sinus of the heart and therefore is also referred to as a coronary sinus electrode line. The electrodes for detecting electric potentials in the right ventricle and for delivering right ventricular stimulation pulses are typically attached to a right ventricular electrode line whose distal end protrudes into the apex of the right ventricle. At their proximal end, the electrode lines are typically connected to a corresponding cardiac stimulator via standardized plug connections.

The typical stimulation modes of a right ventricular cardiac stimulator such as VVI, VVD or DDD, for example, may be assumed to be known. The same thing is also true of the delivery of stimulation pulses only in case of need (demand pacemaker) in which delivery of a stimulation pulse to a particular chamber of the heart is suppressed when a particular characteristic action (intrinsic contraction) of the respective heart chamber has been detected in a corresponding escape interval via a sensing unit of the cardiac stimulator assigned to this ventricle of the heart. These essentially known concepts may also be implemented with the cardiac stimulator described here.

BRIEF SUMMARY OF THE INVENTION

The cardiac stimulator here is a biventricular cardiac stimulator, which is essentially capable of stimulating both ventricles of the heart continuously or on demand.

The goal of the present invention is to create a cardiac stimulator which can switch automatically between a biventricular stimulation mode for cardiac resynchronization therapy and a right ventricular stimulation mode—hereinafter also referred to as the normal mode—in alternation. Depending on the embodiment of the cardiac stimulator, it is designed to operate in essentially known modes, i.e., also in a hysteresis mode, for example, in the normal mode in which only the right ventricle is stimulated and this is done only on demand, if necessary, e.g., to operate in the frequency hysteresis or AV-time hysteresis or in a VP suppression mode in which delivery of ventricular stimulation pulses is fundamentally inhibited.

According to the present invention, the object of creating a cardiac stimulator which automatically switches back and forth between a biventricular stimulation mode and a right ventricular stimulation mode is achieved by the fact that the cardiac pacemaker has not only the known right and left ventricular sensing units and stimulation units but also has a stimulation unit designed to always switch the cardiac stimulator to the right ventricular stimulation mode in which no left ventricular stimulation pulses are delivered whenever the duration of a respective prevailing QRS signal interval is shorter than a first reference value and to switch it to a biventricular stimulation mode in which both the right and left ventricles can be stimulated when the duration of a prevailing QRS signal interval is longer than a predefined second comparison value. The first and second reference values may be identical here. The duration of the QRS signal interval denotes the duration of the essentially known QRS complex in an electrocardiogram.

The cardiac stimulator is preferably designed to derive a signal representing the respective QRS signal interval from the respective intrinsic VV interval, which represents the period of time between a right ventricular contraction of the heart detected by the right ventricular sensing unit and the respective left ventricular contraction of the heart detected by a left ventricular sensing unit.

As an alternative to that, the cardiac stimulator may also be designed so that the signal representing the period of the QRS signal interval is also determined as a function of a particular atrioventricular conduction time (AV interval) detected. This may be either the period between a right atrial contraction detected and the respective right ventricular contraction or the period between a right atrial contraction detected and the respective left ventricular contraction. The cardiac stimulator therefore additionally has at least one atrial sensing unit. If the cardiac stimulator is also designed to stimulate the right atrium, it also has a right atrial stimulation unit.

One advantage of such a biventricular cardiac stimulator is that it also expands the scope of use of cardiac stimulators to include patients who could not previously be treated adequately. Whenever patients only occasionally have symptoms that are indications for use of a biventricular cardiac stimulator in the biventricular stimulation mode, it is desirable to be able to offer this stimulation mode but at the same time to also make available the pure right ventricular stimulation mode. In other words, it has been found that preference is essentially given to the pure right ventricular stimulation mode. The biventricular stimulation may lead to a normalization of the heart rhythm in that biventricular stimulation is then no longer necessary. Patients with an intermittent left bundle branch block also benefit from a biventricular cardiac stimulator, which can switch automatically between a biventricular stimulation mode and a right ventricular stimulation mode. Another advantage is that continuous stimulation of right and left ventricles requires much more energy than stimulation of the right ventricle alone and then only on demand. Automatic switching to the right ventricular stimulation mode thus contributes toward energy-efficient operation of the cardiac stimulator and therefore prolongs its lifetime.

Previous cardiac stimulators have allowed only manual switching between a biventricular stimulation mode and a right ventricular stimulation mode by a physician.

Advantageous embodiments of the inventive cardiac stimulator pertain to details about the automatic switching. For example, as already indicated, two different reference values may be provided for the automatic switching, resulting in a hysteresis, or the same reference value may be provided for switching from the right ventricular stimulation mode to the biventricular stimulation mode and vice versa. Furthermore, the cardiac stimulator may be designed to perform switching to the other stimulation mode when the value detected goes either above or below the respective reference value once. Alternatively and preferably, however, the cardiac stimulator is designed to perform switching only when the value measured is either above or below the respective reference value for a predefined number of cardiac cycles in a row.

Other advantageous embodiments relate to providing a VP suppression mode and saving the points in time of the respective switching between one of the stimulation modes in a suitable memory unit. This memory unit is preferably connected to a telemetry unit, which allows the data stored in the memory unit to be transmitted by wireless transmission to an external device and from there optionally transmitted further to a central service center. In this way, the switching points in time between the stimulation modes may be ascertained by remote query, for example.

In addition, automatic switching between the stimulation modes (right ventricular and biventricular) may also be performed as a function of other variables to be detected by the cardiac stimulator, e.g., the ejection fraction, which is essentially known, or the mitral reflux. The stimulation control unit is preferably designed to switch from a right ventricular stimulation to a biventricular stimulation either when the measured ejection fraction falls below a programmable threshold value or when the mitral reflux exceeds a programmable threshold value. If both parameters are analyzed by the cardiac stimulator at the same time, then it switches from a right ventricular mode to a biventricular mode either when the ejection fraction drops below the programmed threshold value or when the mitral reflux exceeds the programmed threshold value. Switching from a biventricular stimulation mode to a right ventricular stimulation mode takes place when the measured ejection fraction is above a programmed second (hysteresis) threshold value for the ejection fraction and the mitral reflux is simultaneously below a programmed second (hysteresis) threshold value for the mitral reflux.

Additional advantageous embodiments are derived through a combination of the features described here with one another and with features known from the state of the art.

BRIEF DESCRIPTION OF THE DRAWINGS

The invention will now be explained in greater detail on the basis of an exemplary embodiment with reference to the figures, in which.

DETAILED DESCRIPTION OF THE INVENTION

Figure 1:
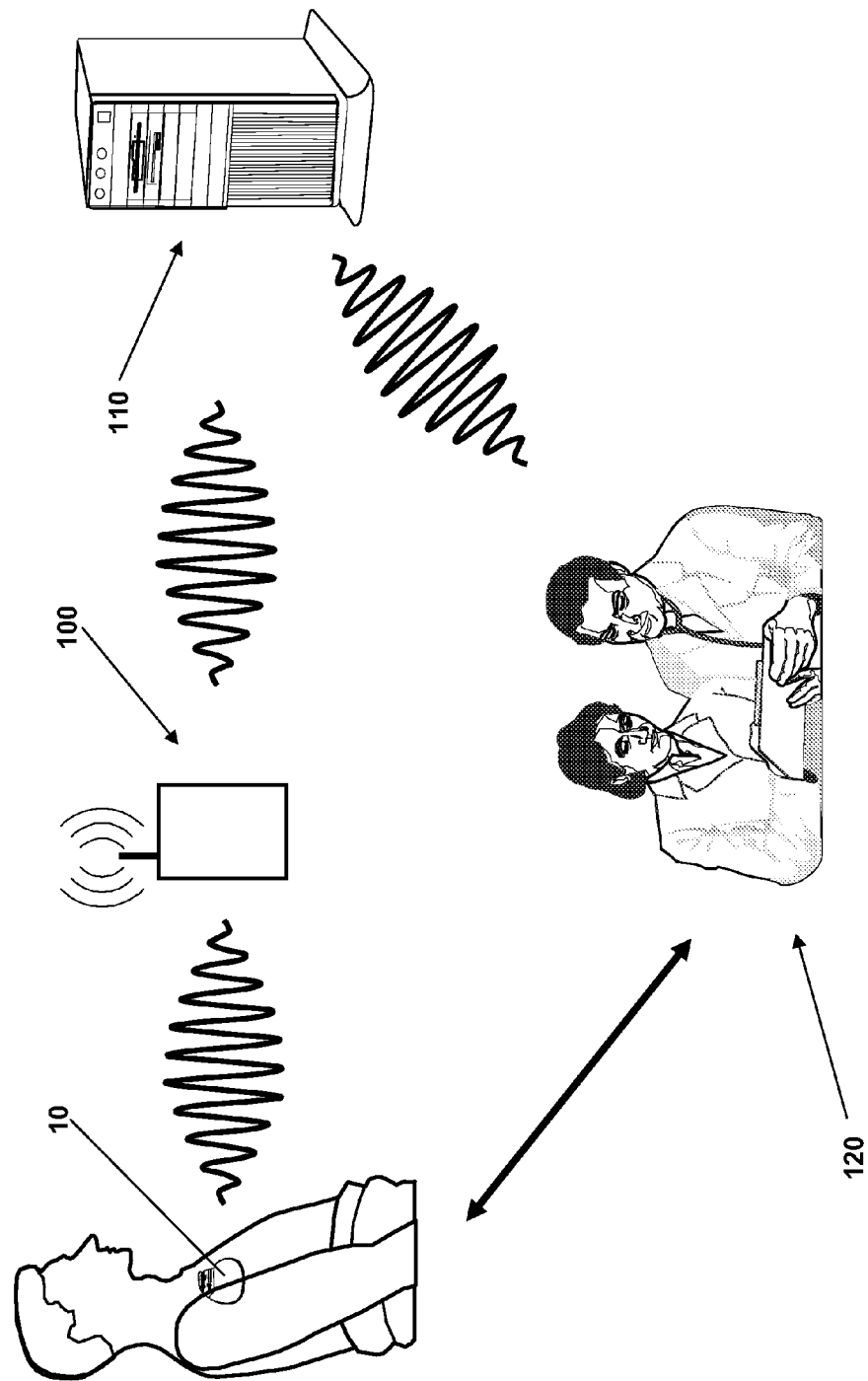
FIG. 1: shows a schematic diagram of a cardiac therapy system.

FIG. 1 shows an overview of a cardiac therapy system which comprises, in addition to an implanted cardiac pacemaker 10, an external device (patient device) 100 and a service center 110, represented symbolically by a server. The implantable cardiac stimulator 10 has a telemetry unit for which it is able to exchange data by wireless transmission with an external device 100. The external device 100 is connected to the service center 110 by wire, for example, so that on the whole, data may be exchanged between the service center 110 and the implantable cardiac stimulator 10 via the external device 100 as a relay station. A medical team 120 can inspect the data obtained by the service center 110 from the implantable cardiac stimulator 10 by means of technical data access to the service center 110.

Figure 2:
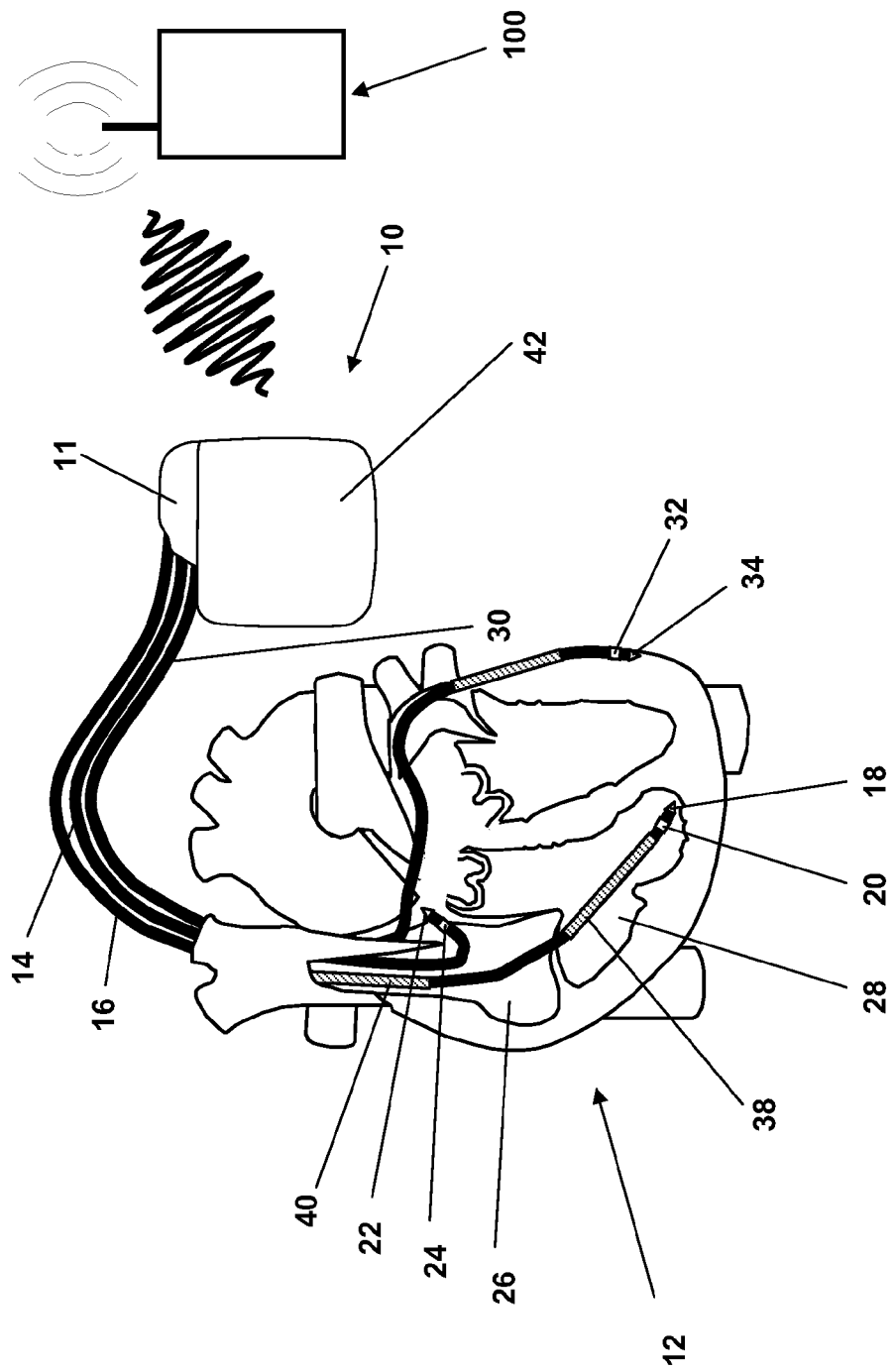
FIG. 2: shows a diagram of a cardiac stimulator with connected electrodes positioned in the heart.

FIG. 2 shows the implantable cardiac stimulator 10 in the form of a triple-chamber cardiac pacemaker/cardioverter/defibrillator with electrode lines 14, 16 and 30 connected to the former and to a heart 12. Furthermore, the external device 100 is also shown near the implantable cardiac stimulator 10. The electrode lines 14, 16 and 30 are electrically connected to contact bushings in a header (connection housing) 11 of the cardiac stimulator 10 by means of known standardized plug connections. In this way, the electrode lines 14, 16 and 30 are also connected to electronic components in the interior of a hermetically sealed metal casing 42 of the cardiac stimulator 10. These components are shown schematically in detail below and determine the inventive functioning of the cardiac stimulator 10.

The electrode line 14 is a right atrial electrode line and has an atrial tip electrode RA tip 22 and at a short distance therefrom an atrial ring electrode RA ring 24, both of which are placed in the right atrium 26 of the heart 12.

The electrode line 16 is a right ventricular electrode line and has a right ventricular tip electrode RV tip 18 on its distal end and a right ventricular ring electrode RV ring 20 in the immediate vicinity. The two electrodes are arranged at the apex of the right ventricle 28 of the heart 12.

Furthermore, the right ventricular electrode line 16 is also a right ventricular shock coil RV shock 38 as a large-area electrode for delivering relative shocks. Another shock coil 40 is provided in the superior vena cava and is therefore also referred to below as the SVC shock electrode.

The electrode line 30 is a left ventricular electrode line on whose distal end a left ventricular tip electrode LV tip 34 is arranged and in the vicinity of which a left ventricular ring electrode LV ring 32 is also arranged. Furthermore, the left ventricular electrode line 30 has a left ventricular shock coil, which is shown in FIG. 2 but is not identified more specifically, for delivering defibrillation shocks to the left ventricle. The left ventricular electrode line 30 leads from the right atrium 26 of the heart 12 out into a lateral vein branching off from the coronary sinus and is therefore also referred to as the coronary sinus electrode line or CS electrode line.

Figure 3:
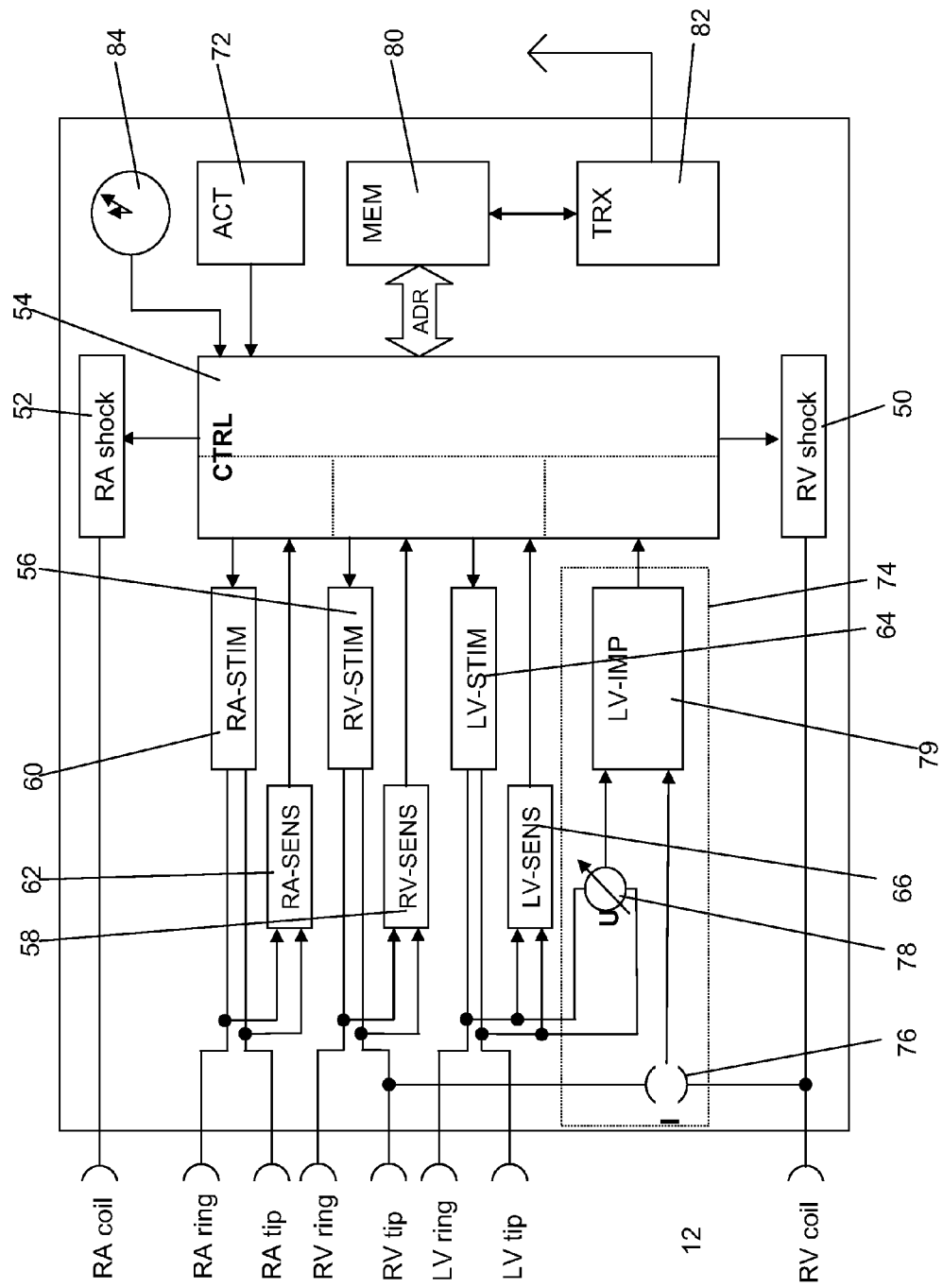
FIG. 3: shows a schematic block diagram of a cardiac stimulator.

FIG. 3 shows the main components of the cardiac stimulator 10. The electric terminals for the various electrodes 18, 20, 22, 24, 32, 34, 38 and 40 are shown on the left side. The shock electrodes 38 and 40 are each connected to a right ventricular shock pulse generator 50 and/or SVC shock generator 52. The two shock generators 50 and 52 are connected to a stimulation control unit 54, triggering both shock pulse generators 50 and 52 to generate and deliver a defibrillation shock as needed.

The connection for the right ventricular tip electrode RV tip and the connection for the right ventricular ring electrode RV ring are each connected to both a right ventricular stimulation unit 56 and to a right ventricular sensing unit 58. Both the right ventricular stimulation unit 56 and the right ventricular sensing unit 58 are connected to the stimulation control unit 54.

The right ventricular stimulation unit 56 is designed to generate a right ventricular stimulation pulse in response to a triggering signal of the stimulation control unit 54 and to deliver this pulse via the terminal for the right ventricular ring electrode and the right ventricular tip electrode. Alternatively, it is also possible for the housing 42 of the cardiac stimulator 10 to form a neutral electrode and for the right ventricular stimulation unit 56 to be connected to the terminal for the right ventricular tip electrode RV tip and the housing 42 as the other electrode for delivering a stimulation pulse. A right ventricular stimulation pulse differs from a defibrillation shock in that the stimulation pulse has a much lower pulse intensity, so it does not stimulate the entire heart tissue (myocardium) of a heart chamber like a defibrillation shock but instead stimulates only the myocardial cells in the immediate vicinity of the right ventricular tip electrode 18. This excitation then propagates through natural stimulus conduction over the entire ventricle and thus ensures a stimulated contraction of the ventricle.

The right ventricular sensing unit 58 is designed to first amplify, through an input amplifier, electric potentials applied at the terminal for the right ventricular ring electrode RV ring and the right ventricular tip electrode RV tip and then to filter them. In addition, the right ventricular sensing unit is designed to analyze the characteristic of the electric signals applied at its inputs, such that the right ventricular sensing unit 58 automatically detects a natural (intrinsic) i.e., automatic contraction of the right ventricle. This may occur, for example, by comparing the characteristic of the signal applied to the inputs of the right ventricular sensing unit 58 with a threshold value. The largest amplitude of the signal in the form of the so-called Z wave is typically characteristic of a natural contraction of the right ventricle, which is detectable by a comparison of threshold values. The right ventricular sensing unit 58 then outputs a corresponding output signal, indicating a natural contraction of the right ventricle, to the stimulation control unit 54.

Similarly, the terminal for the right atrial tip electrode and the terminal for the right atrial ring electrode are connected to both a right atrial stimulation unit 60 and to a right atrial sensing unit 62, each of which is in turn connected to the stimulation control unit 54. The right atrial stimulation unit 60 is designed to generate stimulation pulses, the intensity of which is sufficient to excite the right atrial myocardium. The right atrial stimulation pulses may have a different pulse intensity than the right ventricular stimulation pulses. The right atrial sensing unit 62 is designed to detect a so-called P wave from the characteristic of the differential signal applied at its inputs, said P wave characterizing a natural (intrinsic) contraction of the right atrium. If the right atrial sensing unit 62 detects a corresponding P wave, it generates an output signal which characterizes a natural contraction of the right atrium and forwards it to the stimulation control unit 54.

Similarly, the terminal for the left ventricular tip electrode LV tip and the terminal for the left ventricular ring electrode LV ring are connected to a left ventricular stimulation unit 64 and a left ventricular sensing unit 66. The left ventricular stimulation unit 64 and the left ventricular sensing unit 66 are likewise connected to the stimulation control unit 54. The two units function like the stimulation units 56 and 60 and the sensing units 58 and 62 already described.

As another component of the cardiac stimulator 10, an activity sensor 72 is connected to the stimulation control unit 54. The activity sensor 72 is designed to detect a signal that depends on a patient's physical activity, e.g., a motion signal, and to output to the stimulation control unit 54 a corresponding signal indicating physical activity on the part of the patient. This allows the stimulation control unit 54 to adjust the timing of the stimulation pulses to the needs of the patient (hemodynamic demand).

In addition, an impedance measuring unit 74 by which a pulsed measurement current can be output by means of a current source 76 via the right ventricular tip electrode (terminal RV tip) and the right ventricular shock coil (terminal RV coil). A voltage measuring unit 78 measures the resulting drop in voltage. An impedance analyzing unit 79 is designed to form an impedance signal from this. For delivery of this impedance signal, it is connected to the stimulation control unit 54. With the help of the impedance measuring unit 54, such variables as the ejection fraction (EF) or—with a different electrode configuration accordingly—the mitral reflux (MR) can be determined advantageously and taken into account by the stimulation control unit 54 for optimization of the timing of the stimulation pulses.

In addition, the cardiac stimulator 10 comprises a memory unit 80 which is connected to the stimulation control unit 54 and allows storage of the signals generated or analyzed by the stimulation control unit 54. On the other hand, the memory unit 80 allows control programs for the stimulation control unit 54 to be saved in a modifiable form. In addition, the stimulation control unit 54 is connected to a timer 84.

The memory unit 80 is connected to a telemetry unit 82, which makes it possible to transmit data stored in the memory unit 80 to the external device 100 by wireless transmission or to transmit program commands on the part of the external device 100 to the cardiac stimulator 10 and store them in the memory unit 80.

As a triple-chamber cardiac stimulator/cardioverter/defibrillator, the cardiac stimulator 10 is able to perform a stimulation of the right atrium, the right ventricle and the left ventricle or even just one or two of these chambers of the heart in a known manner. This includes in particular stimulation of a respective heart chamber in demand mode, in which stimulation pulses are delivered to the respective heart chamber only if no intrinsic contraction of the respective heart chamber is detected on the part of the respective sensing unit in a previous respective escape interval. The cardiac pacemaker is thus capable of performing the known right ventricular stimulation modes such as VVI, VVD or DDD. In addition, the cardiac pacemaker is preferably able to provide escape intervals of different lengths for stimulation of the right ventricle, depending on whether or not an intrinsic contraction of the ventricle was detected in the previous escape interval. If intrinsic contractions of the ventricle occur regularly, preference is given to a longer right atrial escape interval to give priority to the intrinsic rhythm of the heart. This prolonged right ventricular escape interval is somewhat longer than would be physiologically appropriate. A shorter physiologically appropriate right ventricular escape interval is always selected automatically if no right ventricular intrinsic action of the heart is detected, so that the right ventricle is stimulated regularly. In this context, there is a known frequency hysteresis in which a corresponding interval between two successive right ventricular events is lengthened or shortened and there is an AV time hysteresis in which the interval between a right atrial event and the next right ventricular stimulation pulse is lengthened or shortened. An event in this context is understood to be a respective contraction of a heart chamber. A natural event is understood accordingly to be an independent natural (intrinsic) contraction of a respective heart chamber and a stimulated event is a contraction of the respective heart chamber attributed to a corresponding stimulation pulse.

The most important property of the cardiac stimulator 10 in the present context consists of its ability to perform cardiac resynchronization therapy (CRT) by stimulation of the right ventricle and the left ventricle. The corresponding stimulation mode is known as the biventricular stimulation mode and is controlled by the stimulation control unit 54. The timing of the stimulation pulses for the right and left ventricle is optimized in a fundamentally known manner, e.g., by taking into account a respective measured ejection fraction (see above) or the mitral reflux (also see above and in EP 06025401.8).

In particular, an interventricular delay time (VV interval) is important for this timing, i.e., the time with which a right stimulation pulse and a left stimulation pulse follow one another (if they are not inhibited in demand mode). This time may be longer than 0, so that the left stimulation pulse follows the right stimulation pulse. The interventricular delay time may be 0, which means that a right ventricular stimulation pulse and a left ventricular stimulation pulse are delivered simultaneously by simultaneous triggering of the right ventricular stimulation unit 56 in the left ventricular stimulation unit 64 by the stimulation control unit 54. The interventricular delay time may also be less than 0, which means that a left ventricular stimulation pulse is delivered before delivery of the respective right ventricular stimulation pulse.

The biventricular stimulation may also be performed in the so-called VP suppression mode, in which right ventricular stimulation pulses are timed but then are not actually delivered, even if they are not inhibited by a prior intrinsic event in demand mode. Variants of an embodiment of such a VP suppression mode suitable for the cardiac stimulator described here are described in detail in the patent application U.S. Ser. No. 11/484,336.

According to the invention, the cardiac stimulator 10 is designed to alternately switch automatically from the stimulation control unit 54 between a right ventricular stimulation mode and a biventricular stimulation mode in a controlled manner. According to the invention, the stimulation control unit 54 performs this switching in such a way that the stimulation control unit first generates a signal indicating the duration (also referred as the "width" based on the graphic display of an ECG) of a QRS complex. The signal interval of a cardiogram designated as the QRS complex is essentially known. This signal interval is referred to below as the QRS signal interval. The corresponding signal indicating the duration of this QRS signal interval might be determined by the stimulation control unit 54, e.g., by analyzing an intracardiac electrogram (IEGM), such as that picked up by the right ventricular sensing unit 58, for example. The stimulation control unit 54 preferably determines the signal which indicates the duration of the QRS signal interval by determining the natural interventricular conduction time (intrinsic VV interval) in that the stimulation control unit 54 determines the interval in time between a contraction of the right ventricle (intrinsic right ventricular event) detected by the right ventricular sensing unit 58 and a contraction of the left ventricle (left ventricular event) that is to be assigned causally to the right ventricular contraction detected by the left ventricular sensing unit 66. Alternative preferred embodiments of the stimulation control unit 54 for determining the duration of the signal indicating the QRS signal interval consist of the stimulation control unit 54 determining this signal as the atrioventricular conduction time, which is the duration between a contraction of the right atrium detected by the right atrial sensing unit 62 and a contraction of the right or left ventricle detected by the right ventricular sensing unit 58 or the left ventricular sensing unit 66.

The stimulation control unit 54 is designed to compare the signal which indicates the duration of a QRS signal interval and is determined in this way with a comparison value. The stimulation control unit 54 therefore has a corresponding comparison device.

According to a preferred variant of the embodiment, two different comparison values are provided, a first comparison value being used as the comparison criterion for switching from the biventricular stimulation mode to the right ventricular stimulation mode and a second comparison value being used as the comparison criterion for switching from the right ventricular stimulation mode to the biventricular stimulation mode. The first comparison value corresponds to the comparatively shorter duration of the QRS signal interval as the reference value and the second comparison value corresponds to a comparatively longer duration of the QRS signal interval as the reference value. In this way, the stimulation control unit 54 serves to retain the respective prevailing stimulation mode for a somewhat longer period of time.

A preferred variant of the stimulation control unit 54 serves the same purpose; it is designed to perform switching from one stimulation mode to the other stimulation mode only when the value measured is above or below the respective comparison value for a predefined number of several cardiac cycles.

Figure 4:
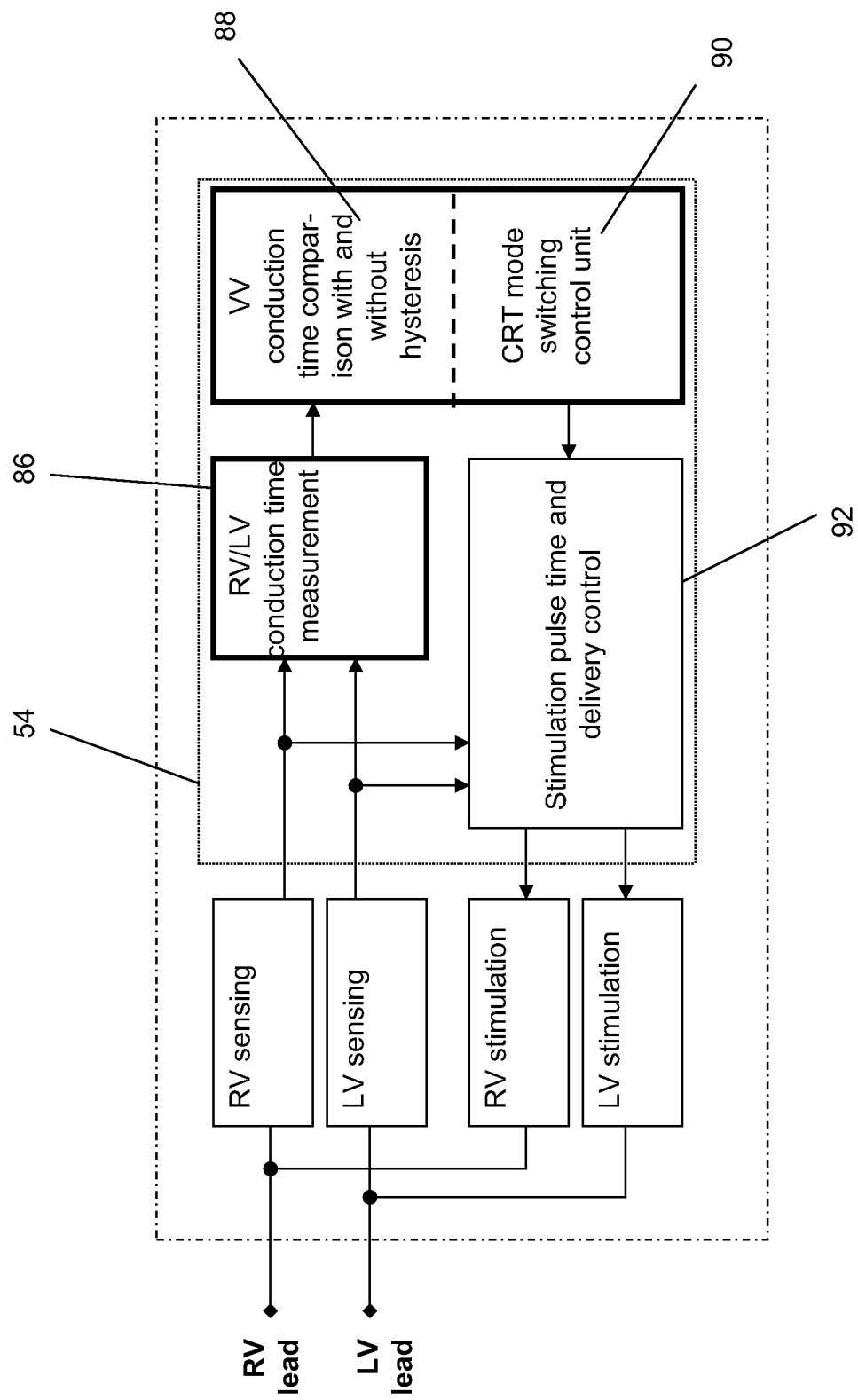
FIG. 4: shows a schematic block diagram to explain the inventive cardiac stimulator in greater detail against the background of the block diagram from FIG. 3.

The illustration in FIG. 4 serves to explain this functioning on the stimulation control unit 54; in addition to the relevant stimulation units and sensing units, it has the following components of the stimulation control unit 54: a VV conduction time measuring unit 86, a VV comparison unit 88, a stimulation mode switch 90 and a stimulation pulse time and delivery control unit 92. The VV conduction time measuring unit 86 cooperates with the timer 84 to determine the intrinsic VV conduction time in the manner described above.

The example in FIG. 4 is based on the variant of the embodiment according to which the stimulation control unit 54 is designed to form the signal which indicates the duration of the QRS signal interval, so that it is proportional to the intrinsic interventricular conduction time.

Figure 5:
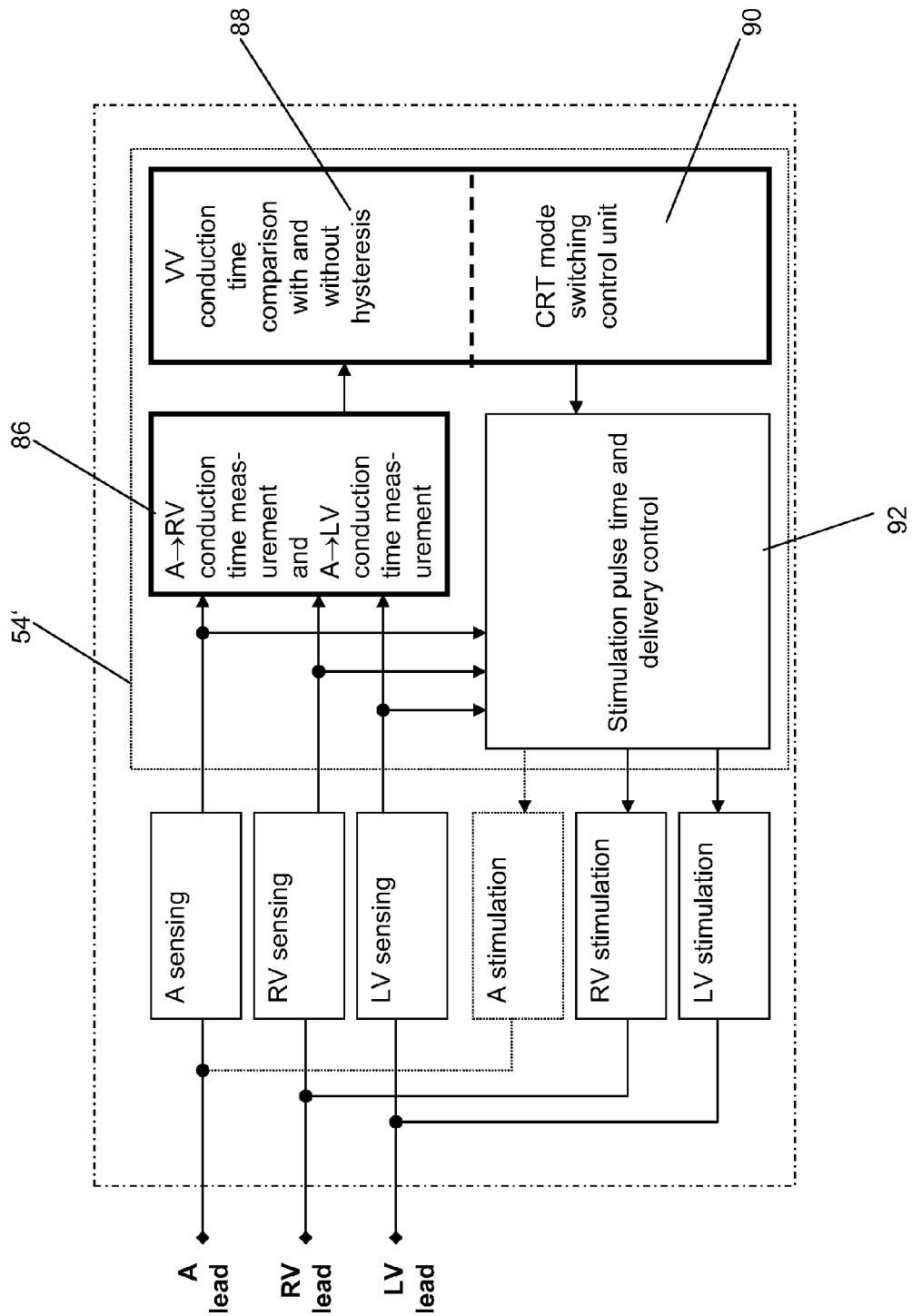
FIG. 5: shows a block diagram of an alternative variant.

FIG. 5 shows an alternative variant of the embodiment according to which the stimulation control unit 54' is designed to form the signal indicating the duration of the QRS signal interval, which is proportional to the atrioventricular conduction time and is proportional either to the conduction time from the right atrium to the right ventricle or to the conduction time from the right atrium to the left ventricle. Accordingly, in the exemplary embodiment according to FIG. 5, the stimulation control unit 54' is also connected to all three electrode lines, namely the right atrial electrode line 14, the right ventricular electrode line 16 and the left ventricular electrode line 30.

Figure 6:
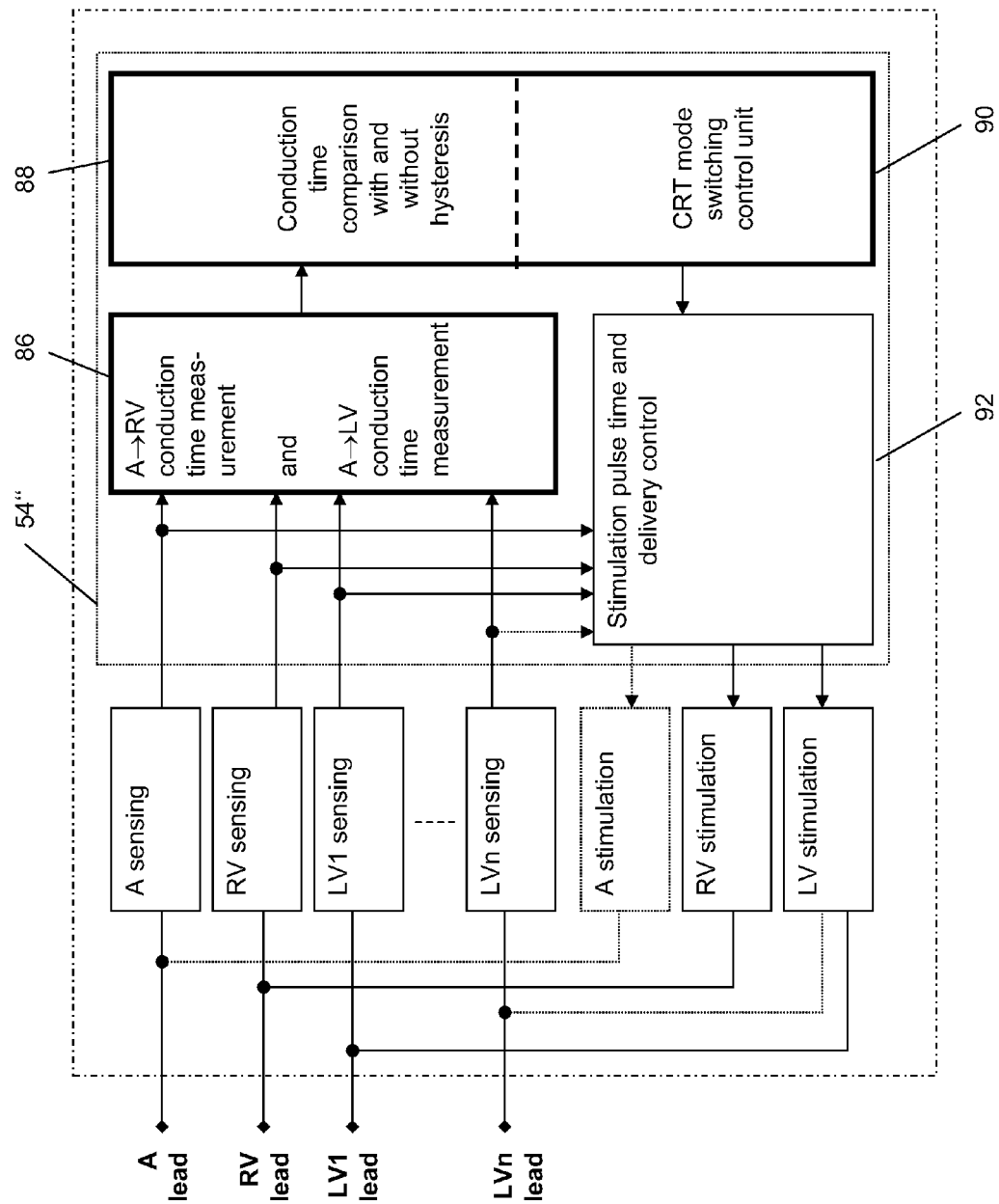
FIG. 6: shows a block diagram of another alternative variant.

FIG. 6 shows an exemplary embodiment, that depicts stimulation control unit 54",which is designed so that not only a single left ventricular electrode line such as the electrode line 30 may be provided but the cardiac stimulator may also be designed to be connected to a plurality of left ventricular electrode lines.

Figure 7:
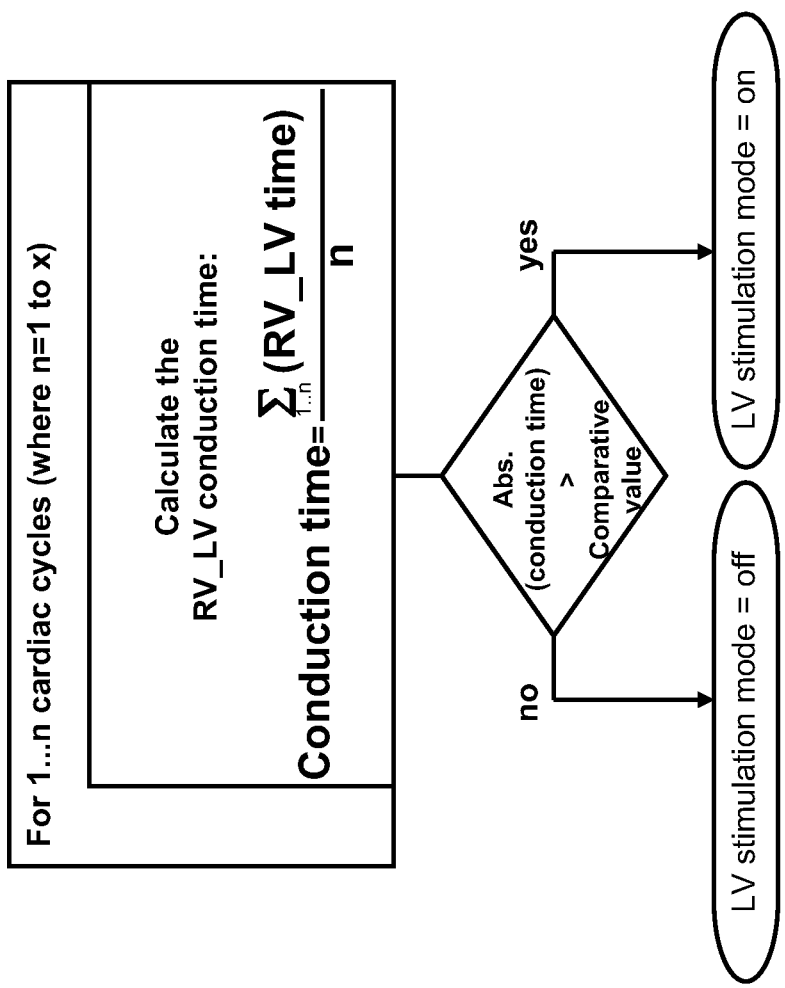
FIG. 7: shows a flow chart to illustrate the functioning of the inventive cardiac stimulator.

Finally, FIG. 7 shows in a flow chart how the stimulation control unit 54 determines the duration of the intrinsic interventricular conduction time (intrinsic VV interval) and then the switching to one or the other stimulation modes takes place. First the average of the interventricular conduction time is formed over multiple cardiac cycles and then the absolute value of the average thereby formed (conduction time) is compared with a single comparison value. If the average of the conduction time thereby formed exceeds this comparison value, then the stimulation control unit 54 switches the cardiac stimulator 10 to the biventricular stimulation mode, in which the left ventricle is also stimulated. However, if the average conduction time is less than the comparison value, the stimulation control unit 54 switches the cardiac stimulator 10 to the right ventricular stimulation mode in which the left ventricle is not stimulated.

Figure 8:
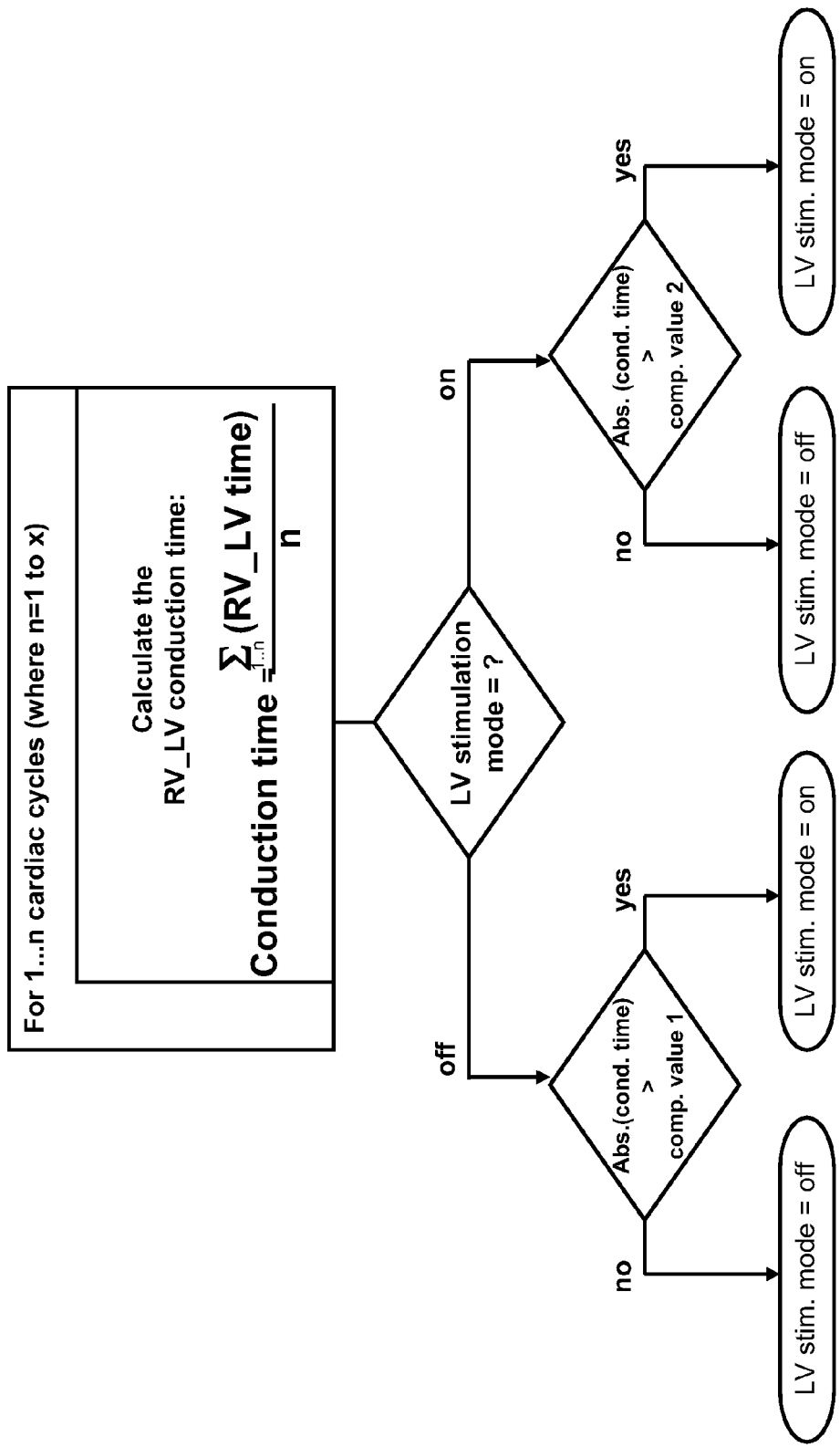
FIG. 8: shows a flow chart of a preferred mode of operation of the inventive cardiac stimulator.

FIG. 8 shows a flow chart of a preferred variant of the invention according to which two different comparison values are provided with which the absolute value of the average of the interventricular conduction time formed over n cardiac cycles is compared, depending on whether the cardiac stimulator 10 is in its biventricular stimulation mode (right branch, comparison with the second comparison value) or in its right ventricular stimulation mode (comparison with the first comparison value).

Figure 9:
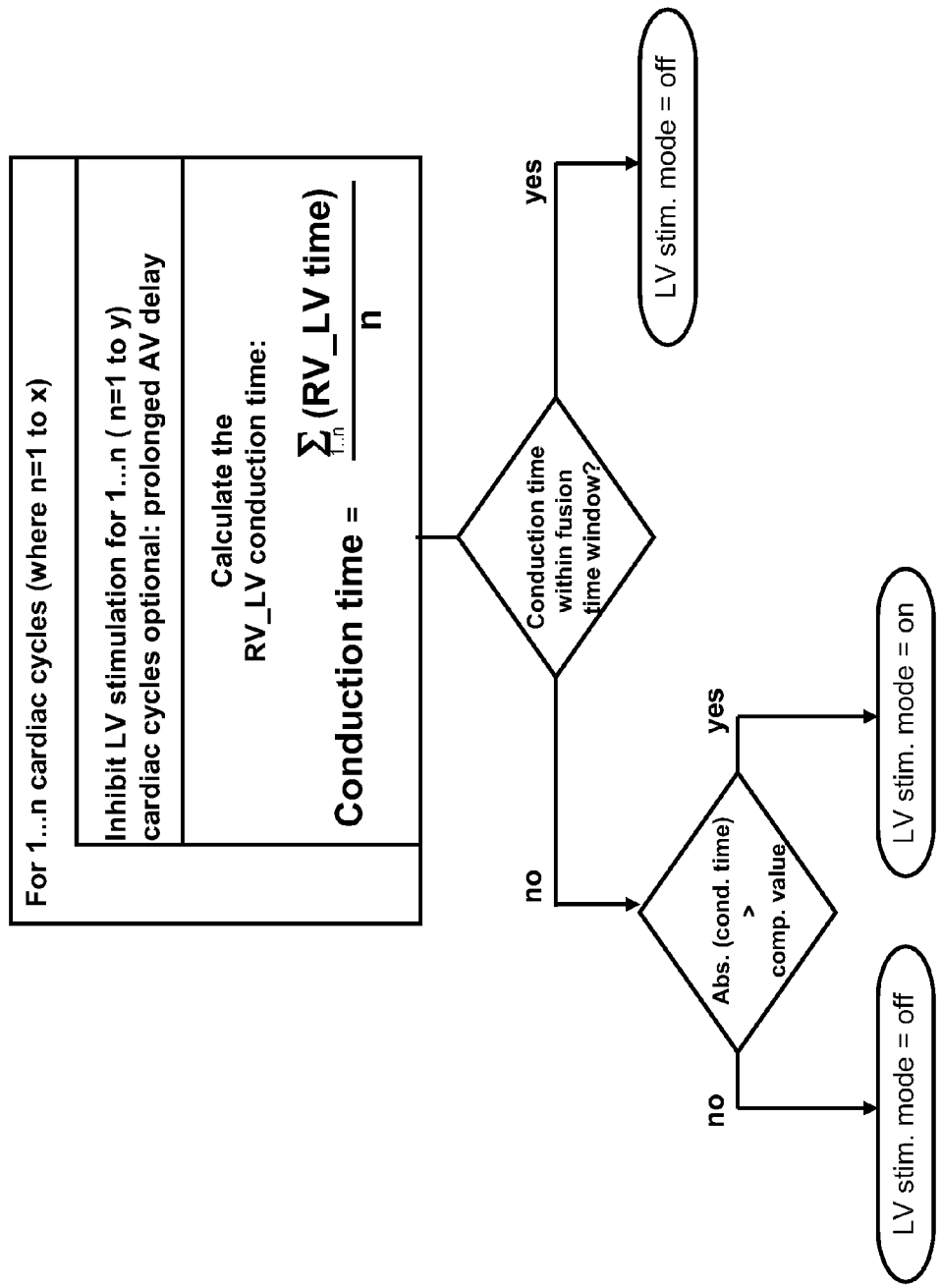
FIG. 9: shows a flow chart to illustrate another alternative mode of operation of the inventive cardiac stimulator.

Finally, FIG. 9 shows a flow chart illustrating how the interventricular conduction time averaged over n cardiac cycles with the left ventricular stimulation deactivated or using a lengthened AV time is compared first with a comparison interval known as a "fusion time window." If the average interventricular conduction time is in this comparison time window, then the stimulation control unit 54 switches the cardiac stimulator 10 to the right ventricular stimulation mode in any case. The fusion time window is a time window which is wrapped around the end of a respective left ventricular escape interval. The left ventricular escape interval is the interval at the end of which a left ventricular stimulation pulse is triggered if this is not inhibited by a previously occurring left ventricular natural event. The left ventricular escape interval is usually started with a right atrial event. The fusion time window is selected so that within the fusion time window there is the risk that a left ventricular stimulation pulse will be delivered at a point in time when a natural left ventricular contraction would also occur, so that there is a so-called fusion event.

Only when the aforementioned comparison of the average interventricular conduction time has shown that it ends outside of the fusion time window does the stimulation control unit 54 perform the comparison of the average interventricular conduction time described above with a comparison and switch either to the biventricular stimulation mode or to the right ventricular stimulation mode, depending on the result of the comparison. The variant of the embodiment depicted in FIG. 9 represents the case in which the average interventricular conduction time is compared with only one comparison value. By analogy with the variant depicted in FIG. 8, this comparison may also be performed with two different comparison values.

Additionally or alternatively, the cardiac stimulator may also be designed to perform the switching between the right ventricular stimulation mode and the biventricular stimulation mode as a function of the measured ejection fraction or the mitral reflux determined or of both variables, such that there is a switch from a right ventricular stimulation to biventricular stimulation either when the measured ejection fraction drops below a programmable threshold level or the mitral reflux exceeds a programmable threshold value. If the two parameters are analyzed by the cardiac stimulator at the same time, switching from a right ventricular mode to a biventricular mode takes place either when the ejection fraction drops below the programmed threshold value or the mitral reflux exceeds the programmed threshold value. Switching from a biventricular stimulation mode to a right ventricular stimulation mode takes place when the measured ejection fraction is above a programmed second threshold value (hysteresis) for the ejection fraction and at the same time, the mitral reflux is below a programmed second threshold value (hysteresis) for the mitral reflux.

List Of Reference Numerals

| Reference numeral | Meaning |
| --- | --- |
| 10 | cardiac stimulator |
| 100 | external device |
| 110 | service center |
| 120 | medical team |
| 11 | standardized contact bushings in a header (terminal housing) |
| 12 | heart |
| 14 | right atrial electrode line |
| 16 | right ventricular electrode line |
| 18 | right ventricular tip electrode RV tip |
| 20 | right ventricular ring electrode RV ring |
| 22 | atrial tip electrode RA tip |
| 24 | atrial ring electrode RA ring |
| 26 | right atrium |
| 28 | right ventricle |
| 30 | left ventricular electrode line |
| 32 | left ventricular ring electrode LV ring |
| 34 | left ventricular tip electrode LV tip |
| 38 | right ventricular shock coil RV shock |
| 40 | shock coil |
| 42 | housing |
| 50 | right ventricular shock pulse generator |
| 52 | SVC shock pulse generator |
| 54 | stimulation control unit |
| 56 | right ventricular stimulation unit |
| 58 | right ventricular sensing unit |
| 60 | right atrial stimulation unit |
| 62 | right atrial sensing unit |
| 64 | left ventricular stimulation unit |
| 66 | left ventricular sensing unit |
| 72 | activity sensor |
| 74 | impedance measuring unit |
| 76 | current source |
| 78 | voltage measuring unit |
| 79 | impedance analyzer unit |
| 80 | memory unit |
| 82 | telemetry unit |
| 84 | timer |
| 86 | VV conduction time measuring unit |
| 88 | VV comparison unit |
| 90 | stimulation mode switch |
| 92 | stimulation pulse time and delivery control unit |

What is claimed is:

1. An implantable cardiac stimulator (10), comprising
at least one right ventricular sensing unit (58) which has a first input that is configured to be connected to a right ventricular electrode line (16) and is configured to analyze a first electric input signal applied to the first input, such that the at least one right ventricular sensing unit detects at least one first signal feature typical of a contraction of a right ventricle and generates a corresponding first output signal;
at least one right ventricular stimulation unit (56) which has a first output that is configured to be connected to the right ventricular electrode line (16) and is configured to generate a right ventricular stimulation pulse in response to a first control signal and deliver the right ventricular stimulation pulse via the first output;
at least one left ventricular sensing unit (66) which has a second input that is configured to be connected to a left ventricular electrode line (30) and and is configured to analyze a second electric input signal applied to the second input, such that the at least one left ventricular sensing unit detects at least one second signal feature typical of a contraction of a left ventricle and generates a corresponding second output signal;

at least one left ventricular stimulation unit (64), which has second output that is configured to be connected to the left ventricular electrode line (30) and is configured to generate a left ventricular stimulation pulse in response to a second control signal and deliver the left ventricular stimulation pulse via the second output;

a stimulation control unit (54) which is connected to the at least one right ventricular sensing unit (58), the at least one left ventricular sensing unit (66), the at least one right ventricular stimulation unit (56) and the at least one left ventricular stimulation unit (64) and is configured to process the first and second output signals of the at least one right ventricular sensing unit (58) and at least one left ventricular sensing unit (66) and to generate the first and second control signals for the at least one right ventricular stimulation unit (56) and the at least one left ventricular stimulation unit (64) to generate near field stimulation pulses sufficient to excite myocardium proximal to a distal end of said right ventricular electrode line and said left ventricular electrode line respectively; and, wherein the stimulation control unit (54) is configured to switch a mode of operation between at least one right ventricular stimulation mode configured to generate near field stimulation pulses in which no control signals to trigger left ventricular pulses are output to the at least one left ventricular stimulation unit, and a biventricular stimulation mode alternately, configured to generate near field stimulation pulses;

wherein the stimulation control unit is additionally configured to switch the mode of operation as a function of a signal that indicates a duration of a prevailing QRS signal interval of a certain signal or any of the first and second electric input signals, such that the stimulation control unit switches to the biventricular stimulation mode configured to generate near field stimulation pulses only when a comparison of the signal that indicates the duration of the prevailing QRS signal interval with a first comparison value reveals that the duration of the prevailing QRS signal interval is longer than a first reference value represented by the first comparison value for a predefined plurality number of cardiac cycles in a row, and switches to the at least one right ventricular stimulation mode configured to generate near field stimulation pulses only when the comparison of the signal that indicates the duration of the prevailing QRS signal interval with a second comparison value reveals that the duration of the prevailing QRS signal interval is shorter than a second reference value represented by the second comparison value for a predefined plurality number of cardiac cycles in a row and, wherein the near field stimulation stimulates only the myocardial cells in an immediate vicinity of the stimulation pulses.

2. The implantable cardiac stimulator according to claim 1, wherein the first and second comparison values and the first and second reference values are each identical.

3. The implantable cardiac stimulator according to claim 1, wherein the stimulation control unit (54) is configured to determine the signal that indicates a duration of a QRS signal interval, so that the signal that indicates the duration of the QRS signal interval reflects an interval of time between the contraction of the right ventricle detected by the at least one right ventricular sensing unit (58) and the contraction of the left ventricle that is to be causally assigned to a right ventricular contraction detected by the at least one left ventricular sensing unit (66).

4. The implantable cardiac stimulator according to claim 1, further comprising:

a right atrial sensing unit (62) which has a third input that is configured to be connected to a right atrial electrode line (14) and is configured to analyze a third electric input signal applied to the third input, such that the right atrial sensing unit (62) detects at least one third signal feature typical of a contraction of a right atrium and generates a corresponding third output signal; and, wherein the stimulation control unit (54) is configured to determine the signal which indicates a duration of a QRS signal interval wherein the signal reflects an interval of time between the contraction of the right atrium detected by the right atrial sensing unit (62) and the contraction of the right ventricle to be assigned causally to a right atrial contraction detected by the at least one right ventricular sensing unit (58).

5. The implantable cardiac stimulator according to claim 1, further comprising:

a right atrial sensing unit (62) which has a third input that is configured to be connected to a right atrial electrode line (14) and is configured to analyze a third electric input signal applied to the third input, such that the right atrial sensing unit (62) detects at least one third signal feature typical of a contraction of a right atrium and generates a corresponding third output signal; and, wherein the stimulation control unit (54) is configured to determine the signal which indicates a duration of a QRS signal interval wherein the signal reflects an interval of time between a contraction of the right atrium detected by the right atrial sensing unit (62) and the contraction of the left ventricle to be assigned causally to a right atrial contraction detected by the at least one left ventricular sensing unit (66).

6. The implantable cardiac stimulator according to claim 1, wherein the stimulation control unit (54) is configured to suppress a delivery of right ventricular stimulation pulses in the at least one right ventricular stimulation mode.

7. The implantable cardiac stimulator according to claim 1, wherein the stimulation control unit (54) is configured to switch from one stimulation mode to another after each time a measured value exceeds or drops below a respective comparison value.

8. The implantable cardiac stimulator according to claim 1, wherein the stimulation control unit (54) is configured to switch from one stimulation mode to another only when the signal that indicates a duration of a QRS signal interval has exceeded or dropped below a respective comparison value for a predetermined number of cardiac cycles.

9. The implantable cardiac stimulator according to claim 1, wherein the stimulation control unit (54) is configured to detect an interval comprising a respective intrinsic VV interval in a biventricular CRT stimulation mode, wherein said interval reflects an interval of time between the contraction of the right ventricle detected by the at least one right ventricular sensing unit (58) and a contraction of the left ventricle to be causally assigned to a right ventricular contraction detected by the at least one left ventricular sensing unit (66), and to determine a left ventricular stimulation point in time that occurs after the end of the respective intrinsic VV interval thereby determined.

10. The implantable cardiac stimulator according to claim 1, wherein the stimulation control unit (54) is connected to a memory unit (80) and is configured to store points in time of the respective switching to switch between stimulation modes in the memory unit (80).

11. The implantable cardiac stimulator according to claim 10, wherein the memory unit (80) is connected to a telemetry unit (82) which is configured to transmit wirelessly data stored in the memory unit (80).

12. The implantable cardiac stimulator according to claim 1, wherein the stimulation control unit is additionally configured to switch the mode of operation as a function of mitral reflux or measured ejection fraction or both said mitral reflux and said measured ejection fraction alone or in combination with said duration of said prevailing QRS signal interval.

13. The implantable cardiac stimulator according to claim 1, further comprising a timer, and wherein the stimulation control unit comprises an intrinsic VV interval conduction time measuring unit, an intrinsic VV interval comparison unit and a stimulation mode switch, such that the intrinsic VV interval conduction time measuring unit is configured to cooperate with the timer to determine an intrinsic VV interval conduction time in a biventricular CRT stimulation mode.

14. The implantable cardiac stimulator according to claim 13, wherein said intrinsic VV interval reflects an interval of time between the contraction of the right ventricle detected by the at least one right ventricular sensing unit (58) and a contraction of the left ventricle to be causally assigned to a right ventricular contraction detected by the at least one left ventricular sensing unit (66), and to determine a left ventricular stimulation point in time that occurs after the end of the respective intrinsic VV interval thereby determined and, wherein the near field stimulation stimulates only the myocardial cells in an immediate vicinity of the stimulation pulses.

15. An implantable cardiac stimulator (10), comprising
at least one right ventricular sensing unit (58) which has a first input that is configured to be connected to a right ventricular electrode line (16) and is configured to analyze a first electric input signal applied to the first input, such that the at least one right ventricular sensing unit detects at least one first signal feature typical of a contraction of a right ventricle and generates a corresponding first output signal;
at least one right ventricular stimulation unit (56) which has a first output that is configured to be connected to the right ventricular electrode line (16) and is configured to generate a right ventricular stimulation pulse in response to a first control signal and deliver the right ventricular stimulation pulse via the first output;
at least one left ventricular sensing unit (66) which has a second input that is configured to be connected to a left ventricular electrode line (30) and and is configured to analyze a second electric input signal applied to the second input, such that the at least one left ventricular sensing unit detects at least one second signal feature typical of a contraction of a left ventricle and generates a corresponding second output signal;
at least one left ventricular stimulation unit (64), which has second output that is configured to be connected to the left ventricular electrode line (30) and is configured to generate a left ventricular stimulation pulse in response to a second control signal and deliver the left ventricular stimulation pulse via the second output;
a stimulation control unit (54) which is connected to the at least one right ventricular sensing unit (58), the at least one left ventricular sensing unit (66), the at least one right ventricular stimulation unit (56) and the at least one left ventricular stimulation unit (64) and is configured to process the first and second output signals of the at least one right ventricular sensing unit (58) and at least one left ventricular sensing unit (66) and to generate the first and second control signals for the at least one right ventricular stimulation unit (56) and the at least one left ventricular stimulation unit (64) to generate near field stimulation pulses sufficient to excite myocardium proximal to a distal end of said right ventricular electrode line and said left ventricular electrode line respectively; and,
wherein the stimulation control unit (54) is configured to switch a mode of operation between at least one right ventricular stimulation mode configured to generate near field stimulation pulses
in which no control signals to trigger left ventricular pulses are output to the at least one left ventricular stimulation unit, and
a biventricular stimulation mode alternately, configured to generate near field stimulation pulses;
wherein the stimulation control unit is additionally configured to switch the mode of operation as a function of a signal that indicates a duration of a prevailing QRS signal interval of a certain signal or any of the first and second electric input signals, such that the stimulation control unit switches to
the biventricular stimulation mode configured to generate near field stimulation pulses only when a comparison of the signal that indicates the duration of the prevailing QRS signal interval with a first comparison value reveals that the duration of the prevailing QRS signal interval is longer than a first reference value represented by the first comparison value for a predefined plurality number of cardiac cycles in a row, and switches to
the at least one right ventricular stimulation mode configured to generate near field stimulation pulses only when the comparison of the signal that indicates the duration of the prevailing QRS signal interval with a second comparison value reveals that the duration of the prevailing QRS signal interval is shorter than a second reference value represented by the second comparison value for a predefined plurality number of cardiac cycles in a row;
a timer coupled with said stimulation control unit;
wherein the stimulation control unit comprises an intrinsic VV interval conduction time measuring unit, an intrinsic VV interval comparison unit and a stimulation mode switch;
such that the intrinsic VV interval conduction time measuring unit is configured to cooperate with the timer to determine an intrinsic VV interval conduction time in a biventricular CRT stimulation mode, wherein said intrinsic VV interval reflects an interval of time between the contraction of the right ventricle detected by the at least one right ventricular sensing unit (58) and a contraction of the left ventricle to be causally assigned to a right ventricular contraction detected by the at least one left ventricular sensing unit (66), and
determine a left ventricular stimulation point in time that occurs after the end of the respective intrinsic VV interval thereby determined.

* * * * *